United States Patent [19]

Jernow et al.

[11] 4,075,209

[45] Feb. 21, 1978

[54] PROCESS FOR PREPARING SUBSTITUTED 2,4-DIAMINOPYRIMIDINES AND ISOXAZOLE INTERMEDIATE

[75] Inventors: Jane Liu Jernow, Verona; Perry Rosen, North Caldwell, both of N.J.

[73] Assignee: Hoffmann-La Roche, Inc., Nutley, N.J.

[21] Appl. No.: 766,094

[22] Filed: Feb. 7, 1977

[51] Int. Cl.$^2$ .................. C07D 239/48; C07D 261/08
[52] U.S. Cl. .......................... 260/256.4 N; 260/307 H
[58] Field of Search ..................... 260/256.4 N, 307 H

[56] References Cited

U.S. PATENT DOCUMENTS

| 3,629,474 | 12/1971 | Ghosh et al. | 260/307 H |
| 3,850,962 | 11/1974 | Grunberg et al. | 260/256.4 N |
| 3,956,327 | 5/1976 | Gresswell et al. | 260/256.4 N |

OTHER PUBLICATIONS

J. P. Tarsio et al., Jr. Org. Chem., 22, 192–193.

*Primary Examiner*—Paul M. Coughlan, Jr.
*Attorney, Agent, or Firm*—Samuel L. Welt; George M. Gold; William G. Isgro

[57] ABSTRACT

A process for the preparation of 2,4-diamino-5-benzyl-pyrimidines by reacting 4-bromomethylisoxazole with an aromatic compound of the formula

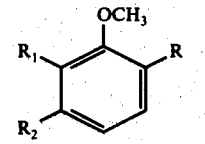

II wherein R, $R_1$ and $R_2$ are hydrogen, lower alkoxy and lower alkyl, and subsequently treating the reaction product with a guanidine salt, is described.

7 Claims, No Drawings

PROCESS FOR PREPARING SUBSTITUTED 2,4-DIAMINOPYRIMIDINES AND ISOXAZOLE INTERMEDIATE

BRIEF SUMMARY OF THE INVENTION

The invention relates to a process for preparing substituted 2,4-diamino-5-benzylpyrimidines of the formula

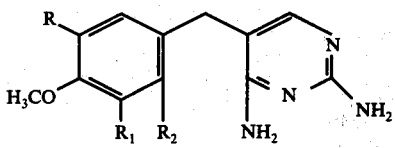

wherein R, $R_1$ and $R_2$ are hydrogen, lower alkoxy and lower alkyl,
by a process which comprises reacting 4-bromomethylisoxazole with an aromatic compound of the formula

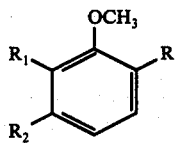

wherein R, $R_1$ and $R_2$ are hydrogen, lower alkoxy and lower alkyl,
whereby a compound of the formula

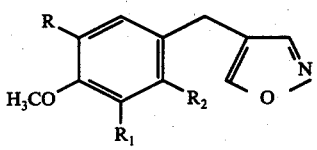

wherein R, $R_1$ and $R_2$ are as described above,
is obtained, and subsequently treating the compound of formula III with guanidine carbonate to obtain the desired end product.

In another aspect, the invention relates to intermediates of formula III.

The 2,4-diamino-5-benzylpyrimidines are known compounds and are useful as potentiators of sulfonamides.

DETAILED DESCRIPTION OF THE INVENTION

As used herein, the term "lower alkyl" denotes a straight or branched chain hydrocarbon group containing from 1 to 7 carbon atoms, for example, methyl, ethyl, propyl, isopropyl, butyl, t-butyl or the like. The term "lower alkoxy" denotes a lower alkyl ether group in which the lower alkyl moiety is as defined above, and includes, for example, methoxy, ethoxy, propoxy, isopropoxy, butoxy, t-butoxy, or the like.

In the process of the invention, the compounds of the formula

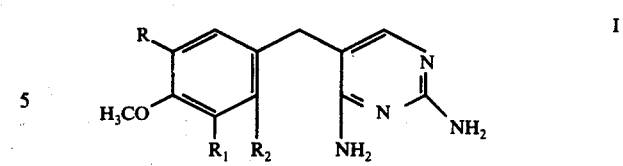

wherein R, $R_1$ and $R_2$ are hydrogen, lower alkoxy and lower alkyl,
are prepared by reacting 4-bromomethylisoxazole with an aromatic compound of the formula

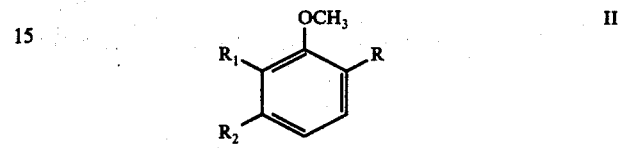

wherein R, $R_1$ and $R_2$ are as described herein,
which results in the formation of an intermediate of the formula

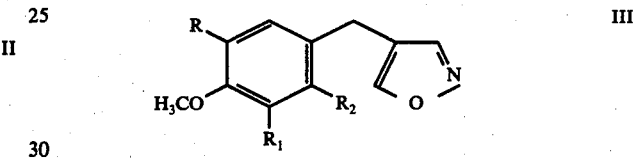

wherein R, $R_1$ and $R_2$ are hydrogen, lower alkoxy and lower alkyl,
which is subsequently treated with a guanidine salt to yield the desired end product.

The 4-bromomethylisoxazole is a known compound and can be prepared according to known procedures, as herein set forth. The compounds of formula II are also known compounds or can be prepared according to known procedures in the art.

The reaction of 4-bromomethylisoxazole with the aromatic compound of formula II comprises a Friedel-Craft reaction. Accordingly, the reaction can be carried out in the presence of a catalyst such as zinc chloride, silver carbonate, silver fluoroborate, stannic chloride and aluminum chloride; zinc chloride is preferred. The intermediate of formula III is obtained by the foregoing reaction.

The compound of formula III is separated from the reaction mixture by conventional methods, such as distillation, chromatography, or the like, and is subsequently reacted with a quanidine salt whose ½ M aqueous solution has a pH in the range of 9 to 12. Preferably, such salts include guanidine carbonate, guanidine acetate, and the like. The foregoing reaction is carried out at the reflux temperature of the reaction mixture; preferably, in the presence of a solvent such as dimethylformamide, or the like. Subsequently, the desired end product of formula I which is formed can be separated according to known procedures, for example, such procedures include distillation, crystallization, or the like. The compounds of formula I which are obtained are known compounds and are useful as antibacterial agents and potentiators of sulfonamides.

The following Examples further illustrate the invention. All temperatures are stated in degrees Centigrade, unless otherwise mentioned.

EXAMPLE 1

Preparation of ethyl 1-propenyl ether

Propionaldehyde diethylacetal was converted to the ethyl enol ether according to the method of Newman et al., J. Org. Chem., 38, 2910 (1973) for the preparation of 2-methoxypropene. Thus, 264 g. of the propionaldehyde diethylacetal was added slowly to a stirred solution of 220 g. of succinic anhydride, 12 g. of benzoic acid, and 16 g. of pyridine in 250 ml. of diglyme at 135°. Approximately 1 hour after the start of the addition, the product began to distill over through a 30 × 6 cm. glass helices packed column while the addition continued. There was 158.5 g. (92%) of distillate (ethyl 1-propenyl ether) collected bp 67°–71°.

EXAMPLE 2

Preparation of 2-methyl-1,1,3,3-tetraethoxypropane

2-Methyl-1,1,3,3-tetraethoxypropane was prepared following the procedure of Protopopova et al., C.A. 51, 11990a (1957) in 81% bp 104°–105° at 10 mm.

EXAMPLE 3

Preparation of 4-methylisoxazole

4-Methylisoxazole was prepared according to the procedure of Burness et al., C.A. 68, 39612e (1968) with the exception of substituting hydroxylamine monosulfonic acid (16% aqueous solution) for hydroxylamine hydrochloride. The product distilled at 124°–126°.

EXAMPLE 4

Preparation of 2,4-diamino-5-methylpyrimidine

A mixture of 1 g. of 4-methylisoxazole and 4.3 g. of guanidine carbonate in 25 ml. of dimethylformamide was stirred at 150° C. for a period of 30 hours. At the end of this period, thin layer chromatography analysis indicated the absence of starting material, and the reaction mixture was allowed to cool and to stand overnight at room temperature. The crude precipitated product was collected, washed with 5 ml. of dimethylformamide followed by 50 ml. of ether, dried and weighed 1.5 g. (100%). Recrystallization from acetone afforded 1.2 g. (80%) of 2,4-diamino-5-methylpyrimidine, mp 183°–185°.

Substituting guanidine acetate and guanidine for guanidine carbonate in the above reaction, resulted in 2,4-diamino-5-methylpyrimidine in 54% and 0% yield, respectively; both reactions were accompanied by extensive decomposition.

EXAMPLE 5

Preparation of 4-(4,5-dimethoxy-2-methylbenzyl)-isoxazole

A mixture of 5.0 g. of 4-bromomethylisoxazole, 180 g. of dimethoxytoluene and a suspension of 4.0 g. of zinc chloride was stirred at room temperature. At the end of 4 hours, the reaction mixture became homogeneous and gas chromatography analysis indicated a two-third conversion of 4-bromomethylisoxazole to 4-(4,5-dimethoxy-2-methylbenzyl)-isoxazole. After having been stirred overnight, the dark colored reaction mixture was poured into a beaker containing 100 ml. of ether and 75 ml. of an aqueous solution of 5% sodium bicarbonate under vigorous mixing. The color of the reaction mixture lightened to a pale yellow. The aqueous layer was separated and extracted with 3 × 100 ml. of ether. The combined organic extracts were dried (sodium sulfate), the solvent removed under vacuo, and the residue distilled to afford 3.4 g. (50%) of 4-(4,5-dimethoxy-2-methylbenzyl)-isoxazole, bp 148°–155° (1 mm.); mp 68.5°–70.5° after recrystallization from ether-hexane.

Anal. Calcd. for $C_{13}H_{15}NO_3$: C, 66.93; H, 6.48; N, 6.01 Found: C, 66.75; H, 6.33; N, 5.80

EXAMPLE 6

Preparation of 2,4-diamino-5-(4,5-dimethoxy-2-methylbenzyl)pyrimidine

A suspension of 1.0 g. of 4-(4,5-dimethoxy-2-methylbenzyl)-isoxazole and 0.774 g. of guanidine carbonate in 6 ml. of dimethylformamide was stirred and heated to reflux. The reaction became homogeneous after ½ hour at the refluxing temperature and was complete (thin layer chromatography) after 6 hours. The mixture was then allowed to cool to room temperature and the stirring continued overnight while the product precipitated. The reaction flask was then kept in an ice bath for a few hours to ensure complete precipitation. The product was collected, washed with 10 ml. of cold dimethylformamide and 10 ml. of cold water, and then air dried to give 0.98 g. of 2,4-diamino-5-(4,5-dimethoxy-2-methylbenzyl)pyrimidine (81%), mp 223°–225°.

EXAMPLE 7

Preparation of 4-(3,4-dimethoxybenzyl)-isoxazole

A mixture of 1.6 g. of 4-bromomethylisoxazole, 1.4 g. of veratrole, and 1.4 g. of zinc chloride was stirred at room temperature overnight. At the end of the reaction period, the deep purple mixture was diluted with ether and an aqueous solution of 5% sodium bicarbonate was cautiously added. The aqueous layer was then extracted with 3 × 100 ml. of ether, the extracts combined and dried (sodium sulfate) and the solvent removed under reduced pressure to yield 2.1 g. of crude 4-(3,4-dimethoxybenzyl)-isoxazole. Dry Column Chromatography (1 part ether; 1 part petroleum-ether) afforded 0.7 g. of pure 4-(3,4-dimethoxybenzyl)-isoxazole as a thick oil.

EXAMPLE 8

Preparation of 4-(3,4,5-trimethoxybenzyl)-isoxazole and 4-(2,3,4-trimethoxybenzyl)isoxazole A mixture of 1.0 g. of 4-bromomethyl-isoxazole, 0.816 g. of zinc chloride and 4 g. of 1,2,3-trimethoxybenzene was heated with stirring at 60° for 3 hours. At the end of this period, thin layer chromatography analysis showed the absence of starting 4-bromomethylisoxazole. The reaction was allowed to cool, diluted with 20 ml. of ether and made basic with a 5% solution of aqueous sodium bicarbonate. The aqueous layer was separated, extracted with 3 × 100 ml. of ether, and the ether extracts combined with the organic layer and dried (sodium sulfate). The solvent was removed under reduced pressure, and the desired products, 4-(3,4,5-trimethoxybenzyl)-isoxazole and 4-(2,3,4-trimethoxybenzyl)-isoxazole were isolated.

We claim:

1. A process for preparing a compound of the formula

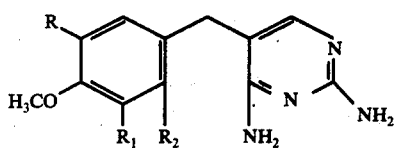

wherein R, R₁ and R₂ are hydrogen, lower alkoxy and lower alkyl, which comprises the steps of (a) reacting 4-bromomethylisoxazole with the corresponding aromatic compound of the formula

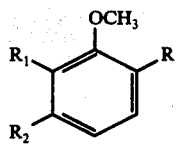

wherein R, R₁ and R₂ are as described above, to yield a compound of the formula

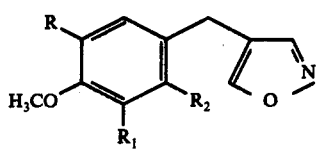

wherein R, R₁ and R₂ are as described above,
and subsequently (b) separating and treating the reaction product of step (a) with a guanidine salt, whose ½ M aqueous solution has a pH in the range of 9 to 12.

2. A process in accordance with claim 1, wherein the guanidine salt is guanidine carbonate.

3. A compound of the formula

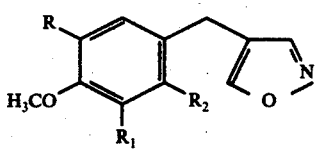

wherein R, R₁ and R₂ are hydrogen, lower alkoxy and lower alkyl.

4. A compound in accordance with claim 3, 4-(4,5-dimethoxy-2-methylbenzyl)isoxazole.

5. A compound in accordance with claim 3, 4-(3,4-dimethoxybenzyl)-isoxazole.

6. A compound in accordance with claim 3, 4-(3,4,5-trimethoxybenzyl)-isoxazole.

7. A compound in accordance with claim 3, 4-(2,3,4-trimethoxybenzyl)-isoxazole.

* * * * *